United States Patent [19]

Poler

[11] 4,080,709
[45] Mar. 28, 1978

[54] METHOD OF MAKING AN INTRA-OCULAR LENS

[76] Inventor: Stanley Poler, 78 E. Second St., New York, N.Y. 10003

[21] Appl. No.: 780,682

[22] Filed: Mar. 23, 1977

Related U.S. Application Data

[63] Continuation-in-part of Ser. No. 691,033, May 28, 1976.

[51] Int. Cl.² .......................... B23P 17/00; A61F 1/16; A61F 1/24
[52] U.S. Cl. ........................................... 29/412; 3/13; 29/450; 29/453; 29/513; 29/509; 29/DIG. 16; 156/645; 156/664; 156/625
[58] Field of Search ................. 29/DIG. 16, 412, 417, 29/20, 450, 453, 462, 509, 513; 3/1, 13; 156/625, 643, 645, 664

[56] References Cited

U.S. PATENT DOCUMENTS

| 2,437,228 | 3/1948 | Mears et al. | 156/645 X |
| 2,754,520 | 7/1956 | Crawford | 3/13 |
| 2,834,023 | 5/1958 | Lieb | 3/1 |
| 3,925,825 | 12/1975 | Richards et al. | 3/13 |
| 3,959,527 | 5/1976 | Droege | 156/645 X |

OTHER PUBLICATIONS

"Artiphakia & Aniseikonia," by Richard Troutman, American Journal of Opthalmology, vol. 56, No. 2, Oct. 1963, pp. 602–639.

Primary Examiner—Victor A. DiPalma
Attorney, Agent, or Firm—Hopgood, Calimafde, Kalil, Blaustein & Lieberman

[57] ABSTRACT

The invention contemplates improved techniques for making lens implants for use in ophthalmological surgery, the lens being a replacement for a cataract-clouded natural lens, and the replacement being installed in the pupil at the iris as the operative step following removal of the cataracted lens. The lens produced by the inventive method features adapter structure assembled to an intra-ocular lens element and having first and second pluralities of radially outward stabilizing feet, in angularly spaced and interlaced relation with the feet of the other plurality; and the respective pluralities of stabilizing feet are on opposite sides of the iris, thus enabling the iris to retain and position the implanted lens.

15 Claims, 18 Drawing Figures

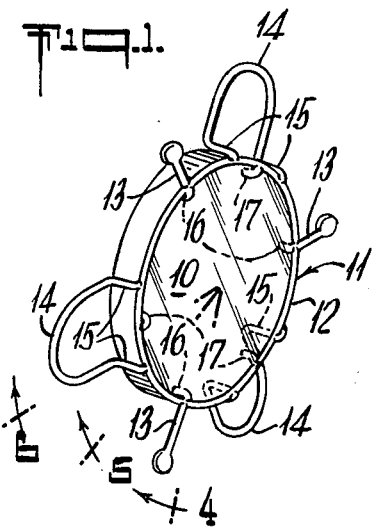
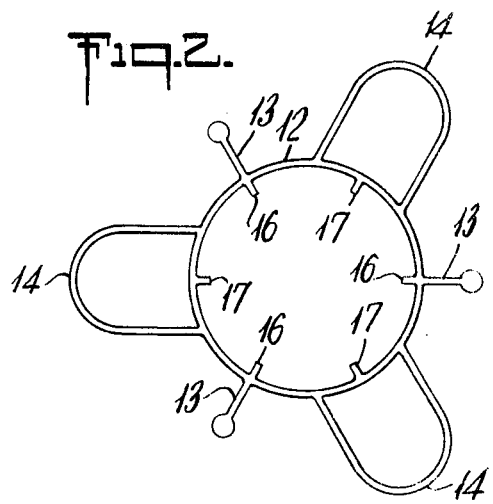
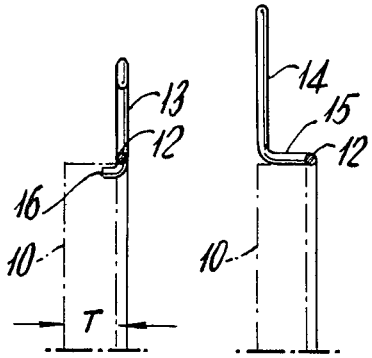
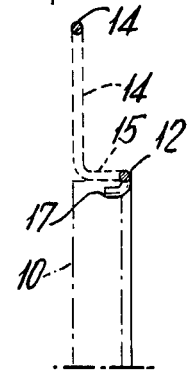
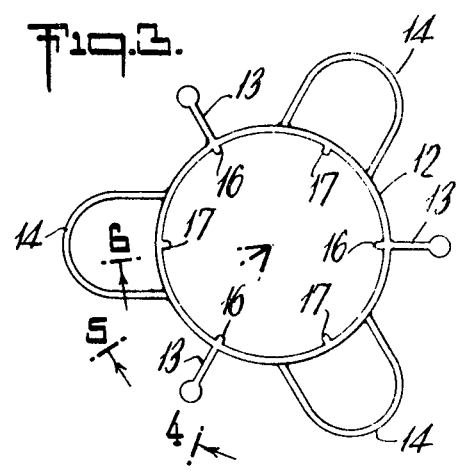
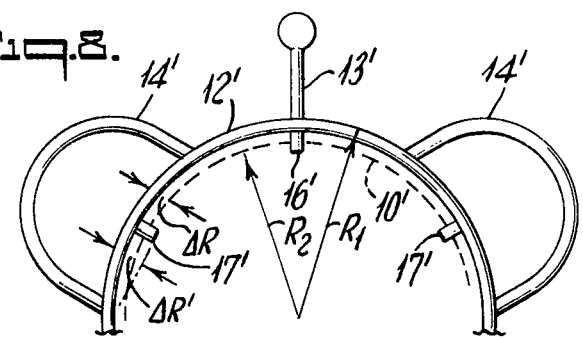
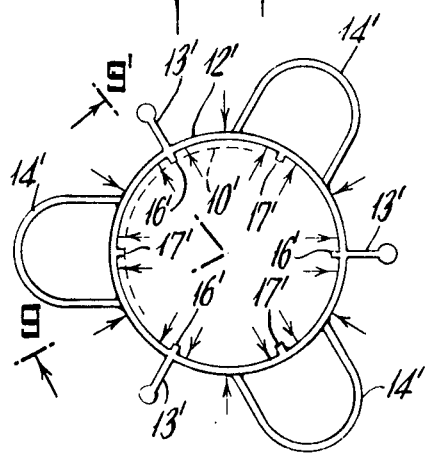
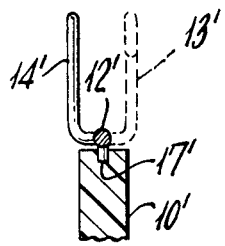
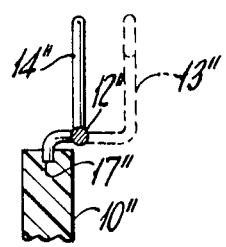

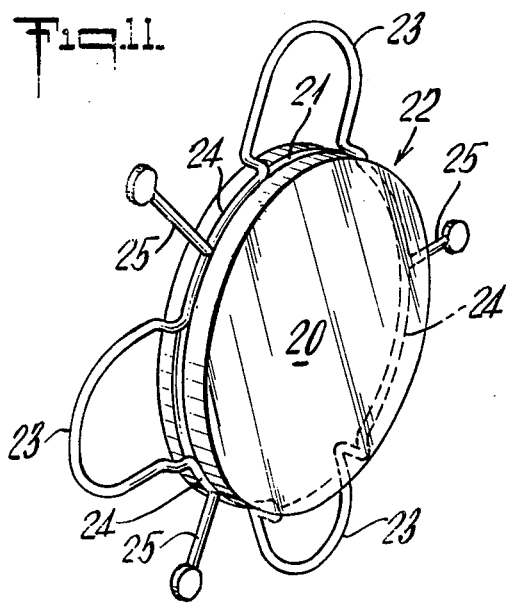
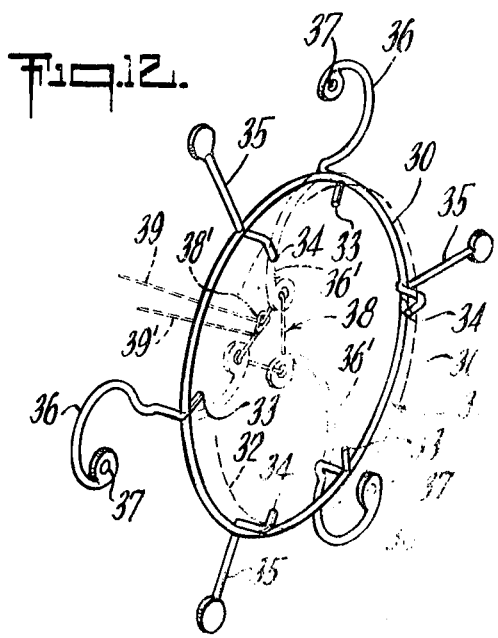
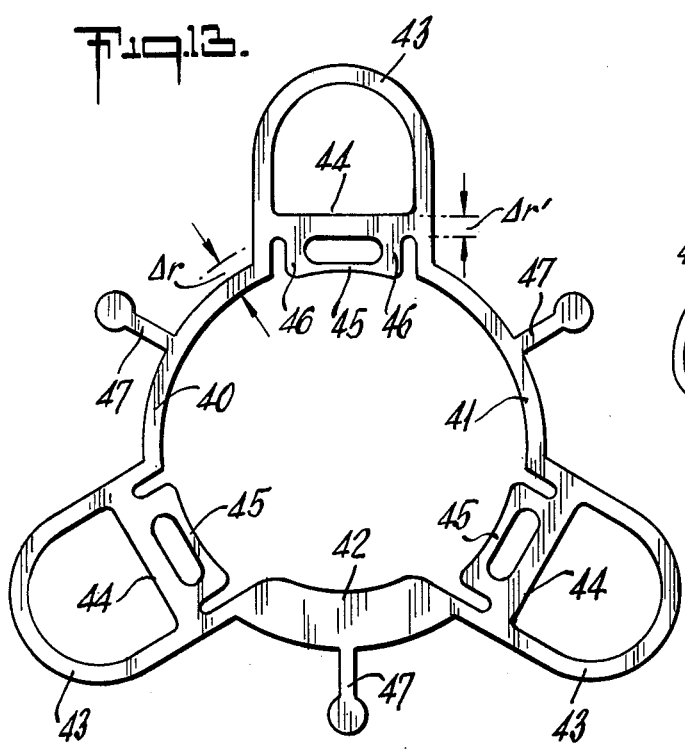
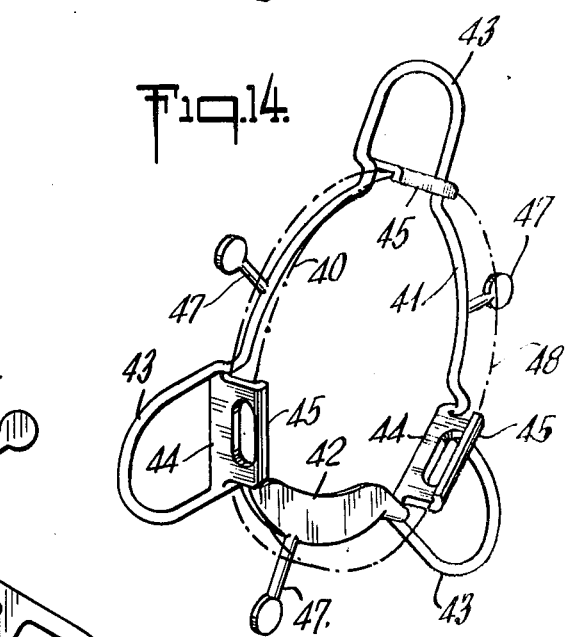
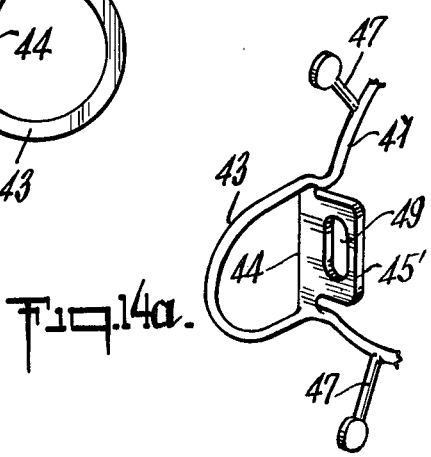

METHOD OF MAKING AN INTRA-OCULAR LENS

This application is a continuation-in-part as to subject matter that is non-elected in my copending application, Ser. No. 691,033, filed May 28, 1976.

The invention relates to methods of making an improved lens implant, as a replacement for a cataract-clouded or otherwise diseased natural lens.

As many as 500,000 Americans a year require surgery for removal of a natural lens which has become opaque (cataract), causing loss of vision. The modern therapy for cataract is surgical removal; this is generally done either by gently lifting the opaque lens from the eye in one piece, or by fragmenting the lens and washing out the fragments. When the cataractous lens is removed, an alternate method must be provided to focus light entering the eye, so that a sharp image focuses at the retina. Strong spectacle lenses and contact lenses are both commonly used for this purpose, but both have important shortcomings. Strong spectacle lenses tremendously enlarge the image, foreshorten distances, restrict peripheral vision, and prevent both eyes from being used simultaneously if both eyes have not had cataract surgery; contact lenses overcome some of these problems but introduce others, involved in insertion, removal and frequent maintenance.

The concept of implanting an intra-ocular lens in place of the removed natural lens is not new, although it is of relatively recent origin. To date, however, a significant limitation on such a procuedure has been the relative unavailability of implant lenses, for their production has relied upon small, craft-style workshops, and lens quality has been less than satisfactory.

It is accordingly an object of the invention to provide an improved method for making intra-ocular lenses, for implant procedures of the character indicated.

Another object is to provide a method for making improved mounting structure for such lenses, whereby operative procedures may be more safely and reliably performed.

It is also an object to provide a method for making such lenses complete with mounting structure, of inherent high quality, adherence to specifications, and reproducibility by precision mass-production techniques.

Other objects and various further features of novelty and invention will be pointed out or will occur to those skilled in the art from a reading of the following specification, in conjunction with the accompanying drawings.

In said drawings, which show, for illustrative purposes only, preferred forms of the invention:

FIG. 1 is an enlarged view in perspective, showing an intraocular lens and unitary mount of the invention, ready for operative implantation, as in the course of a cataract operation;

FIGS. 2 and 3 are plan views of the unitary mount of FIG. 1, FIG. 2 being to show an interim formative condition, and FIG. 3 showing the fully formed mount ready for assembly to the lens element;

Figure 15:
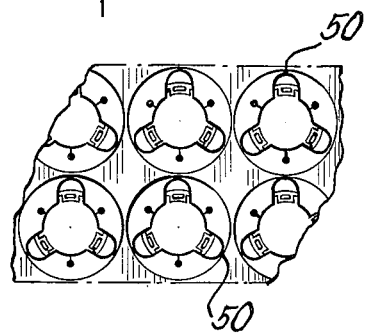
Figure 16:
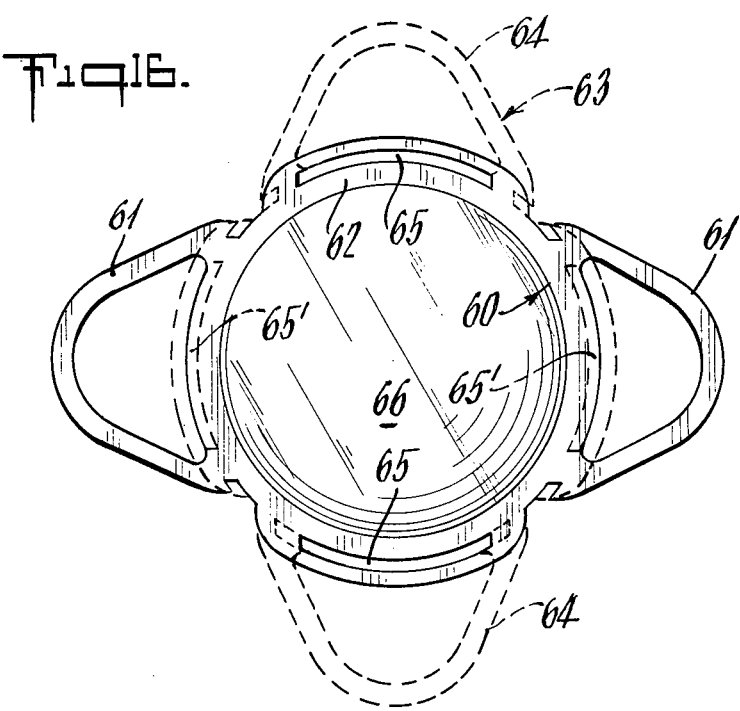
Figure 17:
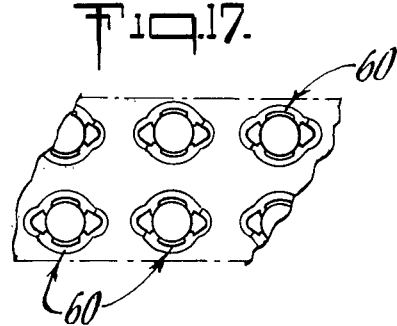

FIGS. 4, 5 and 6 are fragmentary sectional views taken at the planes 4, 5 and 6 indicated in FIGS. 1 and 3;

FIG. 7 is a view similar to FIG. 3 to show a modification;

FIG. 8 is an enlarged fragmentary view of the structure of FIG. 7, to permit identification of dimensional features;

FIG. 9 is a fragmentary sectional view, with solid outlines as taken at the plane 9, and with phantom outlines as taken at the plane 9' of FIG. 7;

FIG. 10 is a view similar to FIG. 9 to show a modification;

FIGS. 11 and 12 are perspective views to show further modifications;

FIGS. 13 and 14 are plan and perspective views to show the blank form and the ultimately bent configuration of a mounting that is particularly adapted to manufacture from a plastic material;

FIG. 14A is a fragmentary view similar to FIG. 14, to show a variation;

FIG. 15 is a fragmentary plan view of a photographically duplicated plurality of lens-mount blanks, in side-by-side severably connected multiple; and FIGS. 16 and 17 are plan and fragmentary plan views similar to FIGS. 14 and 15, to illustrate another application of the method of the invention.

Referring to FIGS. 1 and 6, the invention is shown in application to an implant lens 10 of non-toxic transparent plastic, such as methylmethacrylate. Lens 10 is of such refractive index and is so ground that when mounted at the iris and immersed in the intra-ocular, the thus-implanted eye will develop sharp image focus at the retina. Lens 10 is typically although not necessarily circular about its optical axis; it may, for example, be of 5-mm diameter and have a peripheral-edge thickness T of 1-mm or less.

In accordance with the invention, unitary mounting structure 11 is secured to lens 10 and provides first and second pluralities of radially outward feet for axially stabilized positioning reference to the iris, the feet of one plurality being axially offset from and angularly interlaced with those of the other plurality, so that both sides of the iris contribute to stability. As shown, a circumferentially continuous ring 12 conforms to the peripheral contour of the edge of lens 10, being positioned adjacent one face of the lens. The first plurality of feet comprises three angularly spaced rods 13 extending radially outward for retention adjacent the outer side (anterior surface) of the iris, with the pupilary border of the iris itself closing upon the circular edge of the lens. The second plurality of feet comprises three radially outward loops 14 in a radial plane which is axially offset from ring 12, to substantially the extent T. Thus, each of the feet 14 includes two spaced short offset leg portions 15 which engage the circular edge of lens 10, and the radial loop portion extends from the leg portions 15. For the case of the plastic lens 10 of FIG. 1, six L-shaped anchoring prongs 16–17 extend first radially inwardly and then axially rearwardly, the same being embedded into adjacent rim regions of the lens 10.

The described mounting structure or adapter 11 may be a single piece of metal, with all anchoring prongs 16–17 and stabilizing feet 13–14 integrally formed with the body ring 12. The metal is inert to body tissue and fluids and is suitably stainless steel, of thickness in the order of 0.1-mm. I have found it practical to construct the "blank" of FIG. 2, for the mounting structure 11, by employing photographic and etching techniques.

More specifically, for the case of the "blank" of FIG. 2, a drawing was initially prepared, to greatly enlarged scale, e.g., 40 times. This drawing was photographically reduced to ultimate size, and multiplied at indexed locations to produce a photographic negative with plural reduced images of the drawing. Then, one of a class of metals which was tolerated by the body (e.g., stainless steel, platinum, irridium, etc.) was coated with a photosensitive material. The negative was placed in contact with the photosensitive coat, exposed to light, and then developed in a "photographic reversal", thus removing from the exposed surface those areas which have been exposed to light. The sheet that was left was then placed in a chemical solution (ferric chloride) which etched away unwanted material, leaving only a completed profile of the "blank". The described etching process has the advantage that it tends to produce round, burr-free edges, and it can use materials that are lighter and thinner than anything which to my knowledge and belief has been available to date.

FIG. 2 depicts the "blank" thus prepared, it being noted that lobes 14' are of extended radial projection, in order to account both for the offsets 15 and the loops 14; by the same token, the barbs 16'-17' are of extended inward radial projection, in order to account for both the radially inward and the axially inward leg portions of prongs 16-17. Bending dies are employed to operate upon the "blank" of FIG. 2, such that all necessary axial offsets are produced, resulting in reduction of the overall circle defined by legs 14 and expansion of the circle defined by prongs 16-17, all as appears from comparison of the "before" and "after" plan views of FIGS. 2 and 3.

To complete the description of an actual physical embodiment of FIGS. 1 to 6, I indicate that each of the retaining rod-like feet 13 terminates with a small knob formation, to avoid presentation of any sharp edge to irritate iris tissue. These knobs are on a circle of 7.5-mm diameter, and the outer limits of legs 14 are on a circle of 8-mm diameter. The prongs 16-17 are bent axially at a location radially inwardly offset about 0.15-mm from the body ring 12; they are embedded into lens 10 to the extent of about 0.30-mm in the axial direction. Such embedding may be accomplished without drilling, by axially directed ultrasonic driving impulses applied at prongs 16-17, while ring (12) and leg (13-14) parts of the adapter 11 in damped condition. The optical distortion of lens 10 due to such driven assembly of the adapter to the lens is negligible.

In the embodiment of FIGS. 7 to 9, the layout of the adapter "blank" is generally as described for FIG. 2, with the exception that the radius $R_1$ of the body ring 12' exceeds the radius $R_2$ of the lens 10' about its optical axis to an extent $\Delta R$ which is slightly less than the effective radially inwardly projecting extent $\Delta R'$ of the anchoring barbs 16'-17'. The interlaced pluralities of radially outward stabilizing feet 13'-14' are in axially offset relation, each plurality being offset in the direction opposite the other plurality, as is apparent from FIG. 9. To assemble the adapter of FIG. 7 to its lens 10', the body ring 12' is transiently distorted by suitable tooling, in approach to a polygonal shape; the action of such tooling is denoted by radially inward and radially outward arrows which symbolize local force application to transiently radially outwardly displace all barbs 16'-17' to clear the outer-edge on rim radius $R_2$ of lens 10'. Once axially centered around this rim, the tooling is relaxed to allow compliant restoration, barbs 16'-17' contact the lens rim and are then driven into short radial local embedment in the lens, as by ultrasonic tool means. The assembly is then complete and ready for sterilization and implantation.

FIG. 10 illustrates a slight modification of FIGS. 7 to 9, wherein the ring body 12" is at one axial end of lens 10" and the pluralities of stabilizing feet 13"-14" determine iris retention in a plane that is axially offset from lens 10". The barbs 16"-17" are longer than previously described, to permit an axially offsetting projection from ring 12" before radially inward bending to engage and become locally radially embedded at spaced locations along the rim of lens 10".

In the embodiment of FIG. 11, the rim of lens 20 has a peripheral groove 21, and the unitary mounting adapter 22 is so formed as to permanently assemble by resilient snap action into the groove 21. Adapter 22 may still be formed from a single piece "blank" by the indicated photo-chemical technique, and it may still be a circumferentially continuous structure. As shown, the looped legs 23 comprising one plurality of locating feet integrally connect adjacent ends of spaced body-ring arcs 24, and the rod-like feet 25 of the other plurality extend radially from the respective arcs 24; axial offset of these pluralities is built into legs 23, in the manner generally as described at 15 in FIG. 1, except for a small initial radially outward offset in such legs 23 at juncture with arcs 24. In unstressed condition, the arcs 24 are of curvature conforming to that of groove 21 and are preferably at a slight radially inwardly displaced position with respect to the circle of groove 21. To assemble to lens 20, arcs 24 are outwardly spread against the compliant action of loops 23, in order to permit placement and resilient snap retention of arcs 24 in groove 21. The assembly is then ready for sterilization and implantation.

In the embodiment of FIG. 12, the circular body ring 30 of a unitary adapter 31 is retained in its assembly to a lens 32 by radially inward barbs 33-34 of one plurality (33) which engage over one axial end of lens 32 and of another plurality (34) interlaced with the barbs of the first plurality and engaging over the other axial end of lens 32, thus retaining the assembly without resort to mechanical embedment in lens material.

As shown, the iris-stabilizing feet 35 of one plurality are spaced radial rods at the ring locations of barbs 34, and barbs 34 include axial offsets to the extent of lens-rim thickness. The feet 36 of the other plurality include axial offsets at juncture to the body ring 30, at which locations barbs 33 also extend radially inward. Feet 36 differ from the loops already described in that they are somewhat coiled or looped in a common radial plane, the free end of the coil being apertured at 37. FIG. 12 will be understood to depict the unstressed normal condition and orientation of feet 36.

In accordance with a feature of the invention, the inherent resilient compliance of feet 36 and their apertured ends 37 are employed to facilitate operative insertion through the pupil of the iris. In preparation, a suture 38 such as a filament of nylon is tied with a loop 38' intermediate its free ends 39-39'. The end 39 is threaded through all foot apertures 37 before passing through loop 38' and is then tightened, to radially inwardly compliantly draw all foot ends 37 to within the peripheral confines of lens 30, as denoted by phantom outlines 36' in FIG. 12. In operative insertion of the retracted legs 36 past the pupil, the suture ends 39-39' are held back, the end 39 being tightly held until release when legs 36 are safely behind the iris. Upon release of the end 39, the other end 39' is drawn, thereby first withdrawing the loop 38' and allowing the remaining end 39 to pull out of loop 38' and all apertures 37 before complete removal of the suture.

FIGS. 13 and 14 depict another lens-mount embodiment of the invention wherein the ring-like body comprises plural spaced arcuate spans 40-41-42 between integrally connected loops 43, and wherein at each loop a short bridge 44 (at a radial offset $\Delta r$, with respect to the circle of body arcs 40-41-42, in the blank of FIG. 13) connects the spaced legs of the loop and circumferentially strengthens the circumferential integrity of the body. Radially inwardly extending from each bridge 44 is a lens-retaining formation 45, effectively isolated from the associated bridge 44 except for arcuately spaced integral leg connections 46 thereto. The rod-like feet 47 of previously described embodiments radiate centrally from each of the body arcs 40-41-42.

The blank of FIG. 13 is bent by suitable tooling into the lens-retaining configuration shown in FIG. 14, wherein it is seen that the projections 45 have been axially offset from the plane of body arcs 40-41-42, so that the respective axial limits of the periphery of the lens element (suggested by phantom outline 48) are engaged to permanently retain the lens to its mount. The relatively substantial radial extent $\Delta r'$ by which bridge 44 is connected to the legs of each loop 43, in the context of the relatively torsionally compliant nature of connection of each loop 43 to its adjacent body arc (40-41-42) will be understood to enable transient radially outward manipulation of any of the lens-engaging projections 45 merely by axially deflecting one of the loops 43, thus readily permitting insertion of and engagement to a lens 48 at its rim.

To complete the description of FIG. 14, the loops 43 will be seen also to have been subjected to bending, such that each bridge element 44 extends axially to provide an axial offset for the radial plane of loops 43 with respect to the radial plane of feet 47, so that loops 43 and feet 47 may engage opposite sides of a supporting iris.

Also shown in FIGS. 13 and 14 is the provision of a singularly wide body-arc element at 42, for identification purposes, e.g., manufacturer's mark, lens-identifying code, and date of manufacture.

Thus far, the invention has been described in the particular context of using a metal as the material of the lens-mounting structure. This is not to be taken as precluding the use of other materials, as for example a suitably inert plastic, such as nylon or polypropylene. In a preferred employment of a film sheet of nylon or a high-temperature polyimide (e.g., Kapton, a product of E. I. DuPnt Company), very much the same etching technique may be employed as above indicated for the case of an etched sheet of metal. This close similarity will appear from the following Example I, being a specific recital of steps to produce the plastic article.

EXAMPLE I

1. A sheet of nylon or polyimide film is selected, 0.002 to 0.005-inch thick, being the same thickness range as used in the etched-metal technique described above. The selected plastic sheet is tested for water content, mechanical strength, and spectrographically for fidelity of composition.

2. The sheet is washed in acetone and is then air-dried.

3. The sheet is washed in distilled water and is then air-dried.

4. The sheet is visually inspected for cleanliness and surface defects.

5. The sheet is prepared for a photo-resist coating by vacuum or other deposition of chromium.

6. A photo-resist coating of photographic emulsion is applied to both sides of the sheet and is then allowed to air-dry.

7. By first preparing a drawing at 20X to 50X scale, and then photographically reducing it, in steps as necessary, culminating in reproduction onto a glass photographic plate, a master negative is made to ultimately desired scale; preferably, the master negative includes a plurality of duplicates of the same photographically reduced drawing, in side-by-side adjacency and with interconnected leg formations, as will appear for the tangential rod-like connections 50 to legs of the configuration repeated in FIG. 15.

8. The nylon or polyimide film sheet is placed in a vacuum frame to flatten and hold it tight against a glass platten, and the master negative is photographically exposed to both sides of the sheet, with accurate registry.

9. The exposed sheet is developed, with the result that areas are not developed where masked by the negative and, therefore, not exposed to light. The areas reached by light are washed away by the developer, and in the case of a polyimide sheet, there may be an initial etching action attributable to the developer.

10. The developed sheet is fixed.

11. The sheet is etched, hydrazine hydride being used for the etching of nylon or polyimide sheet, and being usable for certain other plastic materials.

12. The photo-resist is washed away, using either a plasma process or a fluorocarbon cleaner.

13. The resulting lens-mount sheet of severably connected part blanks is then dipped in a 30 percent solution of hydrazine hydride, to round-off edges of the parts.

14. The sheet of otherwise-finished parts is degassed, by increasing sheet temperature to 300° F. in the case of nylon, or 500° F. for the case of high-temperature polyimide.

15. The mounting rings are cut free from the sheet, at 50, to create individual ring blank parts, as in FIG. 13.

16. Individual ring parts are mechanically bent to profile, as appears in FIG. 14, and the profile is inspected.

17. A glass or molded-plastic lens is selected and mounted, as appears from the phantom-outline relation in FIG. 14.

18. The total assembly is inspected, and the assembly is marked, with serial number and code, at 42 in FIG. 14.

19. Final inspection is performed.

20. The total individual assembly is plasma-cleaned and packaged, and then gas or autoclave-sterilized.

21. Final inspection is performed through the package window, and the package is marked, as to date and lot.

A totally different photo-etch or other erosion technique is also applicable to manufacture of lens-mounting adapters of the present character, particularly for the case of such adapters formed from plastic sheet, as will appear from the following Example II.

EXAMPLE II

1. Two matching metal masks or master sheets, for example of aluminum, are prepared as in accordance with the photo-etch technique described at page 5 above.

2. A sheet of suitable plastic, such as nylon or polyimide film, is selected, 0.002 to 0.005-inch thick, and is subjected to tests, washing and drying as noted at steps 1 to 4 of Example I.

3. The metal master sheets are cement-laminated to the front and back surfaces of the plastic sheet, in precise register.

4. The plastic-sheet laminate, thus masked, is exposed to the discharge of a plasma generator or micro-ion mill, in the presence of a suitable reactive gas, for example for one hour, until the desired configuration has been generated by erosion of unmasked regions of the plastic material.

5. The cement is dissolved to permit removal of the aluminum masks or master sheets for cleaning and re-use.

6. The configurated plastic sheet has the appearance of FIG. 15 and may be cleaned by further exposure as in Step No. 4 of this Example II, for example for an exposure time of approximately two minutes, to remove any possible organic debris and burrs.

It will be seen that I have described intra-ocular lens and mount structures meeting all stated objects, and, importantly, lending themselves to mass-production techniques, of inherent precision and control. The drilling operations previously considered necessary have been totally avoided, as has also the reliance upon multiple parts, thus simplifying manufacturing and avoiding generation of waste particles. While plastic lenses have been specifically mentioned in several illustrative contents, it will be appreciated that the invention is not necessarily limited to such use. For example, glass lenses are to be preferred and certainly can be well and safely mounted, using structures of FIGS. 11 to 14. Also, although circular lens body-ring peripheral contours have been described for all forms, it will be appreciated that this was purely to simplify description, in that the described techniques and structures have equal application whatever the peripheral contour of the lens; for example, an oval lens-rim contour may be selected for more ready operative insertion past the pupil, for certain patient requirements, and to reduce the chance of surgical trauma. Still further, the inherent nature of the mounted lenses of the invention is such that an absolute minimum of structure ever protrudes into the anterior chamber of the eye; thus, danger of corneal-tissue contact with any part of the intra-ocular lens structure of the invention is substantially less than that with prior art structures. For the disclosed forms of the invention wherein the iris closes on a circular lens periphery, there is minimal stress on the sphincter muscle, with attendant reduced risk of trauma.

In the discussion thus far, it is has been indicated that the lens element accommodated by my mounting-ring adapter may be of glass or plastic material, the implication being that the lens element is a separate article of manufacture, later assembled to its mount. However, it will be appreciated that every one of the described mounting-ring embodiments is applicable to placement in a suitably formed lens-molding cavity such that at least the lens-retaining part of the mounting ring is embedded in a plastic lens element that is injection-molded in the cavity. The blank of FIG. 13 lends itself particularly well to such use at the time of injection-molding the lens element, in that the lens-retaining extension 45 need not be bent radially, as shown in FIG. 14, but rather may merely be bent axially, as shown at 45' in FIG. 14A, in which case injection-molding lens material may be forced in the molding process to enter the slot or opening 49 between bridge 44 and extension 45. Thus-molded, the lens element will be positively keyed and located by radially outwardly formed lens material at each of the openings 49.

It has also been indicated above that the preferred process of etching developed regions of a photographically reduced lens-mount master negative lends itself to quantity production of pluralities of such lens mounts, in adjacent multiple as suggested in FIG. 15. And such production lends itself to further options in regard to assembly with plastic lens elements. In one procedure, the individual mounting blanks are severed at 50 and are then bent to form lens-retaining projections, as described at 45' in connection with FIG. 14A; the individual mount, thus-prepared, may then be assembled to the lens-molding cavity for localized embedding in the lens material in the course of injection-molding the lens. Alternatively, the lens-retaining projections 45' may be bent out of all lens-mount structures in a large plurality on a single sheet, prior to severance at 50; in that event, and with the sheet of thus-formed lens mounts suitably introduced to a multiple-cavity mold for simultaneously molding a similarly spaced plurality of lens elements, all of the plural lens-and-mount assemblies may be completed in a single injection-molding step, i.e., a single injection-molding of all lens elements, each into assembled relation with its own mount. Thus formed, the plural assemblies are conveniently handled, shipped and stored as a single sheet, with severance of individual assemblies at 50, only when and as needed.

While the invention has been described in detail for the preferred forms shown, it will be understood that modifications may be made within the scope of the invention. For example, the reference to metal for the adapter structures of FIGS. 11 and 12 will be understood to be illustrative, since similarly formed and suitably stiff and non-toxic plastics may also serve the same purpose. Also, the reference to photo-chemical preparation of metal "blanks" is illustrative of a preferred technique, in that photo-resist and plating techniques of the printed-circuit technology, with subsequent release from a substrate, may also be employed; and the use of positive and negative terminology in reference to photographic processing will be understood to be illustrative and not limiting, in that reversal development techniques for proceeding from positive original, directly to a positive-developed image, are also to be understood as applicable.

Also, while metal-ring structures have been disclosed in combination with the lens element thereby mounted, it will be understood that such unitary structures may be, and in certain cases preferably are, subjected to an inert protective coating of a plastic material such as nylon, thus assuring against any possibility of a minute metal burr or barb projecting for body-tissue contact. By the same token, the described plastic-sheet embodiments and methods will be understood to relate to basic structural formations and not necessarily to be concerned with such final coating or finishing as may be desired for particular purposes; for example, a coating of inert material, such as vacuum-deposited or sputtered Teflon or platinum may be applied to an otherwise-finished configurated adapter element, to provide enhanced assurance of a non-toxic ultimate product.

Still further, it will be understood that although all mounting adapters thus far described have been of single-piece unitary construction, the described methods of manufacture are also applicable to multiple-piece mounting adapters, such as the two-piece configurations disclosed in greater detail in my patent application Ser. No. 780,445 filed on even date herewith. The basic blank element, i.e., for one half of such structure, is shown at 60, in solid outline in FIG. 16, with its two mounting lobes 61 projecting radially outward of its ring-like body 62, at diametrically opposed locations; another such element 63 is shown in phantom outline with its two mounting lobes 64 in angularly interlaced relation with lobes 61. The lobes (61) of one adapter element (60) and the lobes (64) of the other adapter element (63) are retained in slotted interlobe regions 65-65' of the respective elements 60-63, and the thus-assembled adapter elements uniquely locate and retain a lens 66; when inserted in the eye, the lobes 61 stabilize the assembly with reference to one side of the iris, and the lobes 64 provide stability with reference to the other side of the iris. The nature of the material of the elements 60-63 should be such that at least the lobes to be inserted past the iris are resiliently compliant, and highly satisfactory assemblies may be made wherein both adapter elements 60-63 are duplicates of each other, formed of suitable plastic such as nylon or polyimide sheet, according to methods as described above at Example I and Example II. Thus a single multiple-element sheet, a fragment of which is shown in FIG. 17, may be prepared to serve the mounting-adapter element (60-63) purposes of a plurality of FIG. 16 assemblies. It is to be understood, furthermore, that chemical etching and mechanical, electronic or other erosion are to be deemed equivalent manipulative steps, depending upon the manufacturing approach and selected materials involved.

I claim:

1. The method of making an intra-ocular lens mount, which comprises preparing to greatly enlarged scale of a drawing a unitary flat blank for the mount, said drawing being of configuration defining a ring-like body with radially inward barbs at angularly spaced locations and with radially outward feet at angularly spaced locations, photographically reducing said drawing to a negative of intended ultimate scale for the mount, selecting a thin sheet of a metal which is tolerated by the body and coating a surface thereof with photosensitive material, contact-exposing the negative to the photosensitive coating, and developing the same to a positive image upon the metal sheet, subjecting the developed side of the metal sheet to an etching chemical solution, whereby a completed blank results consistent with the positive image configuration, and bending some of the radially outward feet into axially offset relation with respect to others of the radially outward feet.

2. The method of claim 1, additionally including the step of bending at least some of said barbs out of the plane of said blank and into lens-retainable formations axially offset from said plane.

3. The method of making an intra-ocular lens mount, which comprises preparing to greatly enlarge scale of a drawing a unitary flat blank for the mount, said drawing being of configuration defining a ring-like body with radially inward lens-retaining projections at angularly spaced locations and with radially outward feet at angularly spaced locations, photographically reducing said drawing to a negative of intended ultimate scale for the mount, selecting a thin sheet of a plastic material which is tolerated by the body and coating a surface thereof with photosensitive material, contact-exposing the negative to the photosensitive coating, and developing the same to a positive image upon the plastic sheet, subjecting the developed side of the plastic sheet to an etching chemical solution, whereby a completed blank results consistent with the positive image configuration, and bending some of the radially outward feet into axially offset relation with respect to others of the radially outward feet.

4. The method of claim 3, additionally including the step of bending at least some of said lens-retaining projections out of the plane of said blank and into lens-retaining formations axially offset from said plane.

5. The method of claim 3, in which the plastic material is a polyimide.

6. The method of claim 3, in which the plastic material is selected from the group comprising polyamides, polyimides, and polypropylene.

7. The method of claim 3, in which the etching chemical consists essentially of hydrazine hydride.

8. The method of making an intra-ocular lens-mount element, which comprises preparing to greatly enlarged scale of a drawing a unitary flat blank for the element, said drawing being of configuration defining a ring-like body with radially inward lens-retaining means and with radially outward feet at angularly spaced locations, photographically reducing said drawing to a negative of intended ultimate scale for the element, selecting a thin sheet of an etchable material which is tolerated by the body and coating a surface of said material with photosensitive material, contact-exposing the negative to the photosensitive coating, and developing the same to a positive image upon said sheet, subjecting the developed side of said sheet to an etching chemical solution, whereby a completed blank results consistent with the positive image configuration, and bending some of the radially outward feet into axially offset relation with respect to other portions of said blank.

9. The method of making an intra-ocular lens, which comprises selecting an intra-ocular lens element, preparing to greatly enlarged scale of a drawing a unitary flat blank for a mount for the selected lens element, said drawing being of configuration defining a ring-like body with radially inward lens-retaining projections at angularly spaced locations and with radially outward feet at angularly spaced locations, photographically reducing said drawing to a negative of intended ultimate scale for the mount, selecting a thin sheet of an etchable material which is tolerated by the body and coating a surface thereof with photosensitive material, contact-exposing the negative to the photosensitive coating, and developing the same to a positive image upon said sheet, subjecting the developed side of said sheet to an etching chemical solution, whereby a completed ring-body blank results consistent with the positive image configuration, bending some of the radially outward feet into axially offset relation with respect to others of the radially outward feet, and assembling the selected lens element into retained relation with said radially inward projections.

10. The method of claim 9, in which the selected lens element is of glass, an in which the assembling step involves bending at least some of said radially inward projections into axially offset relation to other portions of the ring-body blank, and with said bent projections and said other portions engaging opposite axial sides of the lens element.

11. The method of making an intra-ocular lens, involving a lens element and an adapter mount for iris-stabilized implantation, which method comprises preparing to greatly enlarged scale of a drawing a unitary flat blank of the mount, said drawing being of configuration defining a ring-like body with radially outward feet at angularly spaced location, photographically reducing said drawing to a negative of intended ultimate scale for the mount, selecting a thin sheet of an etchable material which is tolerated by the body and coating a surface thereof with photosensitive material, contact-exposing the negative to the photosensitive coating, developing the same to a positive image upon the sheet, subjecting the developed side of the sheet to an etching chemical solution, whereby a completed ring-like blank results consistent with the positive image configuration, and injection-molding the lens element with the ring-like blank peripherally embedded therein.

12. The method of claim 11, in which said negative is one of a plurality of adjacent duplicate negatives of the same photographically reduced drawing, said negatives being in side-by-side adjacency on a single sheet, with at least one of the feet of adjacent negatives interconnected, said sheet of etchable material being contact-exposed to said single sheet of plural negatives, whereby plural interconnected ring-like body blanks are produced by the etching step, said injection-molding step being performed in multiple while said blanks are interconnected, and thereafter severing the connection of individual mounted lens assemblies.

13. The method of claim 12, in which for each of said interconnected bodies some of the radially outward feet are bent into axially offset relation with respect to others of the radially outward feet in a bending step which is performed prior to the injection-molding of lens elements.

14. The method of making an intra-ocular lens, involving a lens element and an adapter mount for iris-stabilized implantation, which method comprises preparing to greatly enlarged scale of a drawing a unitary flat blank of the mount, said drawing being of configuration defining a ring-like body with radially outward feet at angularly spaced locations, photographically reducing said drawing to a negative of intended ultimate scale for the mount, selecting a thin sheet of an etchable material which is tolerated by the body and coating a surface thereof with photosensitive material, contact-exposing the negative to the photosensitive coating, developing the same to a positive image upon the sheet, subjecting the developed side of the sheet to an etching chemical solution, whereby a completed ring-like blank results consistent with the positive image configuration, said negative being one of a plurality of adjacent duplicate negatives of the same photographically reduced drawing, said negatives being in side-by-side adjacency on a single sheet, with at least one of the feet of adjacent negatives interconnected, said sheet of etchable material being contact-exposed to said single sheet of plural negatives, whereby plural interconnected ring-like body blanks are produced by the etching step, and selecting and assembling individual lens elements to the interconnected body blanks, whereby lens assemblies may remain interconnected until one such assembly is needed at which time it may be severed from its connection to an adjacent assembly.

15. The method of claim 14, in which, prior to lens-element assembly, and at each of said interconnected bodies, some of the radially outward feet are bent into radially offset relation with respect to others of the radially outward feet.

* * * * *